United States Patent [19]

Mallo et al.

[11] Patent Number: 5,258,448
[45] Date of Patent: Nov. 2, 1993

[54] NEW ABSORBENT POLYMERS, MANUFACTURING PROCESS AND THEIR USE IN PARTICULAR FOR SANITARY ARTICLES

[75] Inventors: Paul Mallo, Chatou, France; Fritz Engelhardt; Ulrich Riegel, both of Frankfurt am Main, Fed. Rep. of Germany; Rüdiger Funk, Wiesbaden Naurod, Fed. Rep. of Germany

[73] Assignee: Societe Francaise Hoechst, Puteaux, France

[21] Appl. No.: 957,006

[22] Filed: Oct. 6, 1992

[30] Foreign Application Priority Data

Oct. 11, 1991 [FR] France .................. 91 12552

[51] Int. Cl.$^5$ .................. C08F 8/00
[52] U.S. Cl. .................. 524/556; 524/492; 524/493
[58] Field of Search .................. 524/556, 492, 493

[56] References Cited

U.S. PATENT DOCUMENTS

| | | | |
|---|---|---|---|
| 4,677,135 | 6/1987 | Mishima | 521/62 |
| 4,735,987 | 4/1988 | Morita et al. | 524/436 |
| 5,053,460 | 10/1991 | Mallo et al. | 525/116 |
| 5,098,951 | 3/1992 | Mallo et al. | 525/116 |

FOREIGN PATENT DOCUMENTS

| | | |
|---|---|---|
| 2614027 | 4/1987 | France . |
| 2126591 | 8/1983 | United Kingdom . |

*Primary Examiner*—Paul R. Michl
*Assistant Examiner*—Edward Cain
*Attorney, Agent, or Firm*—Browdy and Neimark

[57] ABSTRACT

Hydrophobic, cross-linked absorbent polymers, insoluble in water, in the form of microbeads, based on silica and acrylic acid partially salified by an alkali metal, are obtained by a polymerization process in a water-in-oil suspension in which an aqueous phase obtained extemporaneously from (1), an aqueous solution containing one or more hydrosoluble polymerization initiators, which are free radical generators, and (2), an aqueous phase containing at a concentration of 50±15% by weight a mixture of by weight 2 to 25% of colloidal silica and 98 to 75% of acrylic acid of which 60 to 80 is salified by an alkaline metal, is introduced slowly, under agitation, into a totally deoxygenated oil phase maintained at boiling point and containing a protective colloid, with an aqueous phase to oil phase weight ratio of between 0.8 and 1.2, then when the polymerization reaction is finished, 15 to 55% of the water present is eliminated by azeotropic distillation with recycling of the organic solvent, then 0.01 to 0.06% in molar proportions relative to the monomers of ethyleneglycol diglycidyl ether is introduced into the reaction mixture at boiling point and azeotropic distillation of the residual water is continued until a suspension is obtained which has a dry content of 85±10% and finally the desired polymer is isolated by filtration; use as absorbent compound and in a sanitary article.

20 Claims, No Drawings

NEW ABSORBENT POLYMERS, MANUFACTURING PROCESS AND THEIR USE IN PARTICULAR FOR SANITARY ARTICLES

The present invention relates to new absorbent polymers, a process for obtaining them and the use of said polymers as an absorbing agent.

Hydrophilic cross-linked polymers which are insoluble in water and based on acrylic acid and an alkali metal acrylate optionally containing mineral filler such as silica are known and they are widely used today in sanitary articles due to their astonishing power for absorbing physiological fluids: urine, blood, etc .... The expanding market for this type of product is always demanding either more effective or more economical or more environmentally-friendly products. In particular, absorbents are sought which do not release the fluids absorbed when they are subjected to pressure.

Now, the Applicant has discovered with astonishment new hydrophilic, cross-linked absorbent polymers, insoluble in water, in the form of microbeads, based on silica and acrylic acid partially salified by an alkali metal. These new very absorbent polymers have absorbent properties which are greater than the products marketed or described at present. In particular, the new polymers are endowed with a very good capacity for absorbing water under load.

This is why a subject of the present Application is new hydrophilic, cross-linked absorbent polymers, insoluble in water, in the form of microbeads, based on silica and acrylic acid partially salified by an alkali metal, characterized by the fact that they can be obtained by a polymerization process in a water-in-oil suspension in which an aqueous phase obtained extemporaneously from on the one hand, an aqueous solution containing one or more hydrosoluble polymerization initiators, which are free radical generators, and on the other hand, an aqueous phase containing at a concentration of 50±15% by weight a mixture containing by weight 2 to 25% of colloidal silica and 98 to 75% of acrylic acid of which 60 to 80% is salified by an alkali metal, is introduced slowly, under agitation, into a totally deoxygenated oil phase maintained at boiling point and containing a protective colloid, with an aqueous phase to oil phase weight ratio of between 0.8 and 1.2, then when the polymerization reaction is finished, 15 to 55% of the water present is eliminated by azeotropic distillation with recycling of the organic solvent, then 0.01 to 0.06% in molar proportions relative to the monomers of ethyleneglycol diglycidyl ether is introduced into the reaction mixture at boiling point and the azeotropic distillation of the residual water is continued until a suspension is obtained which has a dry content of 85±10% and finally the desired polymer is isolated, preferably by filtration.

Within the scope of the present invention, by "microbeads" is meant approximately spherical beads of diameter comprised between 0.05 and 1 mm.

By "insoluble in water" is meant that the polymers contain, at ambient temperature, less than 5% of products soluble in water.

By "alkali metal" is meant sodium and potassium.

The term "silica" designates amorphous colloidal silica, in the form of discrete particles of an average diameter of between about 7 and 150 nm, non-agglomerated between each other by siloxane bonds: Si—O—Si.

At present, it is not known exactly how the colloidal silica is fixed in the polymers of the present invention. It is known, however, that the discrete silica particles are uniformly distributed in the microbeads of the polymers.

Among the polymers according to the present invention, there can be mentioned more particularly the above acrylic acid—alkali metal—silica polymers for which the alkali metal is potassium.

There can also be mentioned those characterized by the fact that the cross-linking is carried out with 0.015 to 0.045% in molar proportions relative to the monomers of ethyleneglycol diglycidyl ether, as well as those characterized by the fact that the oil phase is cyclohexane.

Also a subject of the present invention is a preparation process for hydrophilic, cross-linked absorbent polymers, insoluble in water, in the form of microbeads as defined above characterized by the fact that a polymerization reaction is carried out in a water-in-oil suspension, in an inert atmosphere, by introducing slowly, under agitation, an aqueous phase obtained extemporaneously (preferably as it is introduced) from on the one hand, an aqueous solution containing one or more hydrosoluble polymerization initiators which are free radical generators, and on the other hand, an aqueous phase containing at a concentration of 50±15% by weight, the silica and the monomers chosen, into a completely deoxygenated oil phase, maintained at boiling point and containing a protective colloid, then, when the polymerization reaction is finished, the water, preferably 15 to 55% of it, is partially eliminated by azeotropic distillation with recycling of the organic solvent entrained, then ethyleneglycol diglycidyl ether is introduced in a proportion of 0.01% to 0.06% in molar proportions relative to the monomers in use, into the reaction medium maintained at boiling point, the azeotropic distillation of the residual water is then continued until a suspension is obtained which has a dry content of about 85±10% by weight and finally the desired polymer is isolated, notably by filtration.

The oil phase is constituted by one or more hydrocarbons non-miscible in water, inert vis-a-vis polymerization initiators and capable of providing an azeotrope with the water. There can be mentioned for example petrol fractions with a boiling point of between 50 and 180° C. and notably cyclohexane.

The protective colloid, preferably used at a dose of 0.4 to 2% by weight relative to the weight of monomers, is chosen from those commonly used in this type of polymerization in suspension (cf. Kirk-Othmer, Encyclopaedia of Chemical Technology, 3rd edition, volume 1, page 400). Advantageously, a cellulose ether is chosen, and preferably a cellulose ethylether having an ethoxyl content of 48 to 49.5% (cf. Encyclopaedia of Polymer Science and Engineering, 2nd edition, volume 3, page 254). The protective colloid is preferably previously dissolved or dispersed in the oil phase.

The polymerization reaction is carried out at boiling point of the reaction medium, usually at ambient pressure. It can also be carried out at a pressure lower or higher than ambient pressure.

The polymerization reaction is initiated by one or more hydrosoluble free radical generators; the latter advantageously have a half-life at 70° C. greater than two hours. Such initiation agents are in particular certain mineral peroxides such as sodium peroxodisulphate or certain azo compounds such as 4,4'-dicyano-4,4'- azopentanedioic acid. They are advantageously used in aqueous solution at a concentration of 200 to 3000 ppm relative to the weight of monomers and preferably at a concentration of 500 to 1500 ppm.

The alkali metal acrylate is advantageously obtained in aqueous solution, by direct salification of an aqueous solution of acrylic acid with the corresponding alkali metal hydroxide, preferably potassium hydroxide.

This salification is advantageously carried out at a temperature of between 20° and 35° C. The monomers employed are used in aqueous solution.

The silica is supplied in the form of concentrated aqueous suspensions of amorphous non-agglomerated silica particles such as those marketed by the Applicant under the name "KLEBOSOL".

The aqueous initiation solution and the aqueous phase containing the monomers and the silica at a concentration by weight of 50±15% are mixed extemporaneously, preferably as they are introduced slowly into the agitated oil phase, which is completely deoxygenated and maintained at boiling point by external heating if necessary. The ratio by weight of the aqueous phase to the oil phase is between 0.8 and 1.2, preferably between 0.95 and 1.05 and advantageously this ratio is approximately equal to 1.

The duration of introduction can vary according to the operating units, but generally it is comprised between one and two hours. At the end of the introduction, it is advantageous to maintain the reaction medium at the boiling point for 10 to 60 minutes, under agitation, in order to complete polymerization. Once polymerization is finished, the water present is partially eliminated, preferably 15 to 55%, by azeotropic distillation with recycling of the organic solvent thus entrained, then 100 to 600 ppm, advantageously 150 to 450 ppm in molar proportions relative to the monomers, of ethyleneglycol diglycidyl ether is introduced into the reaction medium maintained at boiling point, and then the elimination of the water present in the reaction medium is continued by azeotropic distillation until a suspension is obtained which has a dry content of 85±10% and the expected product is isolated. As regards this isolation, the suspension can be filtered and the polymer obtained according to the invention process, thus collected, is dried until a dry content greater than 90% is obtained. Thus a cross-linked polymer, insoluble in water, is obtained in the form of microbeads free of fines, with a strong hydrophilic power and a very low content of residual monomers, which are always less than 0.01% by weight.

The hydrophilic properties of the polymers according to the invention are easily determined by a set of simple tests.

Thus, the water absorption capacity of the polymer, designated TG, is determined at 20° C., by agitating 0.4 g of polymer in 500 g of water for 30 minutes, then weighing the drained polymer gel obtained. The weight found is brought to 1 g of dry polymer. The copolymers of the present invention have, in this test, an absorption capacity of the order of 300 to 700 g per gram of dry polymer. By "dry polymer" is meant a polymer with 100% active materials.

The absorption capacity of the salty physiological solution of the polymer, designated TGS, is determined at 20° C., by agitating 2 g of polymer in 500 g of a salty physiological solution for 30 minutes, then weighing the drained polymer gel obtained. The weight found is brought to 1 g of dry polymer. The copolymers of the present invention have, in this test, an absorption capacity of the order of 40 to 70 g per gram of dry polymer.

The content of extractible material, designated TE, is determined according to the following method:

1 g of polymer to be tested is placed in 200 g of salty physiological solution;

this suspension is agitated for one hour at 20° C., then left at rest for 15 hours at 20° C.;

the polymer gel obtained is drained and the filtrate is recovered;

the carboxylic and carboxylate functions present are determined on 100 cm$^3$ of the filtrate;

the result of this determination is expressed in grams of polymer dissolved per 100 g of dry polymer.

In this test, the polymers of the present invention have a content of extractible material of 1 to 5%.

The absorption capacity by capillary action under a load of 15 g per cm$^2$, designated TGC, is determined at 20° C. according to the following protocol: 40 g of Fontainebleau sand with a granulometry of 0.100 to 0.300 mm, 2 g of copolymer to be tested and finally 40 g of Fontainebleau sand are spread successively and uniformly into a cylindrical funnel with a 90 mm diameter filter plate having a porosity of 1. Then a total load of 954 g is placed on the upper layer of sand using a 90 mm diameter glass disk, and the funnel is submerged in a tub containing a constant level of salty physiological solution, so that the level of water totally covers the upper surface of the sintered glass and the quantity of salty physiological solution absorbed by capillary action by the polymer over 90 minutes is measured. The result is expressed in grams of salty physiological solution per gram of dry polymer.

The polymers according to the present invention have useful absorbent properties which justify their use as an absorbing agent and a subject of the invention is also, as absorbing agents, the polymers as defined above, notably for the manufacture of sanitary articles, in particular babies' nappies.

The following examples illustrate the present invention without however limiting it.

EXAMPLE 1

3.5 g of cellulose ethylether, designated CEE, containing 48 to 49.5% of ethoxylated groups and having, at 25° C., a viscosity of 200 mPa.s, in a 5% solution of a toluene - ethanol mixture 80-20 by weight, is dispersed under an inert atmosphere in 635 g of cyclohexane. In this way a dispersion designated D is obtained.

Also, 230 g (3.19 moles) of acrylic acid, designated AA, is dissolved under agitation at a temperature of less than 30° C. in 300 g of an aqueous solution of potassium hydroxide containing 171 g of water and 129 g (2.3 moles) of potassium hydroxide, then 80 g of a silica sol containing 30% by weight of silica in the form of particles which are not linked together, of an average diameter of 13 nm, having a pH of 9 and stabilized with 0.3% by weight of potassium hydroxide, 317 mg of sodium peroxodisulphate dissolved in 10 g of water and finally 13.7 g of water so that the total mass of the aqueous phase is brought to 634 g are introduced successively.

The aqueous phase prepared above is then introduced under agitation, under an inert atmosphere, over 90 minutes into the dispersion D which has been carefully deoxygenated and maintained at boiling point by external heating.

During the introduction of the aqueous phase into dispersion D, an exothermic reaction is observed.

At the end of the introduction, the reaction medium is maintained at boiling point for one hour, then it is subjected to an azeotropic distillation with recycling of the cyclohexane so that about 50 g of water is eliminated.

At this stage, at boiling point and under agitation, 111.4 mg (0.639 mmole) of ethyleneglycol diglycidyl ether is introduced into the reaction medium, then the azeotropic distillation is continued as previously until about 200 g of water is eliminated.

The suspension obtained is then cooled down to ambient temperature, then it is filtered and the precipitate collected is dried in a ventilated oven until it has a dry content of about 96%.

In this way 355 g (341 g expressed as dry product) of an acrylic acid - potassium acrylate - silica polymer is obtained, which is insoluble in water, and is presented in the form of beads of a few tenths of a millimeter in diameter. This polymer has a water absorption capacity, designated TG, of about 310 g/g, and a salty physiological solution absorption capacity, designated, TGS, of about 46 g/g and a salty physiological solution absorption capacity under load, designated TGC, of about 27 g/g. The content of extractible material is 0.7%.

EXAMPLES 2-7

Example 1 is repeated, modifying on the one hand the quantity of water eliminated by azeotropic distillation before the introduction of ethyleneglycol diglycidyl ether, designated PE, and on the other hand the quantity of ethyleneglycol diglycidyl ether used, designated PG. Table I sets out these various quantities as well as the absorption properties of the different polymers obtained.

TABLE 1

| EXAMPLE | PE | PG | TG | TGS | TGC |
|---|---|---|---|---|---|
| 1 | 50 g | 111.4 mg | 310 g/g | 46 g/g | 27 g/g |
| 2 | 130 g | 111.4 mg | 464 g/g | 52 g/g | 24.5 g/g |
| 3 | 181 g | 111.4 mg | 569 g/g | 55 g/g | 24 g/g |
| 4 | 100 g | 167 mg | 326 g/g | 45.5 g/g | 28 g/g |
| 5 | 130 g | 167 mg | 400 g/g | 49.5 g/g | 28.5 g/g |
| 6 | 151 g | 167 mg | 444 g/g | 52 g/g | 27 g/g |
| 7 | 130 g | 167 mg | 401 g/g | 49 g/g | 29 g/g |

We claim:

1. Hydrophobic, cross-linked absorbent polymers, insoluble in water, in the form of microbeads, based on silica and acrylic acid partially salified by an alkali metal, characterized by the fact that they can be obtained by a polymerization process in a water-in-oil suspension in which an aqueous phase obtained extemporaneously from on the one hand, an aqueous solution containing one or more hydrosoluble polymerization initiators, which are free radical generators, and on the other hand, an aqueous phase containing at a concentration of 50±15% by weight a mixture containing by weight 2 to 25% of colloidal silica and 98 to 75% of acrylic acid of which 60 to 80% is salified by an alkali metal, is introduced slowly, under agitation, into a totally deoxygenated oil phase maintained at boiling point and containing a protective colloid, with an aqueous phase to oil phase weight ratio of between 0.8 and 1.2, then when the polymerization reaction is finished, 15 to 55% of the water present is eliminated by azeotropic distillation with recycling of the organic solvent, then 0.01 to 0.06% in molar proportions relative to the monomers of ethyleneglycol diglycidyl ether is introduced into the reaction mixture at boiling point and the azeotropic distillation of the residual water is continued until a suspension is obtained which has a dry content of 85±10% and finally the desired polymer is isolated.

2. Polymers according to claim 1, characterized by the fact that the acrylic acid is salified by potassium.

3. Polymers according to claim 1 characterized by the fact that cross-linking is achieved with 0.015 to 0.045% in molar proportions relative to the monomers of ethyleneglycol diglycidyl ether.

4. Polymers according to claim 1, characterized by the fact that the oil phase is cyclohexane.

5. Preparation process for hydrophobic, cross-linked absorbent polymers, which are insoluble in water, in the form of microbeads, as defined in claim 1, characterized in that a polymerization reaction is carried out in a water-in-oil suspension, in an inert atmosphere, by introducing slowly, under agitation, an aqueous phase obtained extemporaneously from on the one hand, an aqueous solution containing one or more hydrosoluble polymerization initiators which are free radical generators, and on the other hand, an aqueous phase containing at a concentration of 50±15% by weight, the silica and the monomers chosen, into a completely deoxygenated oil phase, maintained at boiling point and containing a protective colloid, then, when the polymerization reaction is finished, the water, preferably 15 to 55% of it, is partially eliminated by azeotropic distillation with recycling of the organic solvent entrained, then ethyleneglycol diglycidyl ether is introduced in a proportion of 0.01 % to 0.06% in molar proportions relative to the monomers in use, into the reaction medium maintained at boiling point, the azeotropic distillation of the residual water is then continued until a suspension is obtained which has a dry content of about 85±10% by weight and finally the desired polymer is isolated.

6. Process according to claim 5, characterized by the fact that the acrylic acid is salified by potassium.

7. Process according to claim 5, characterized by the fact that cross-linking is carried out with 0.015 to 0.045% in molar proportions relative to the monomers of ethyleneglycol diglycidyl ether.

8. Process according to claim 5, characterized by the fact that the oil phase is cyclohexane.

9. Polymers according to claim 2, characterized by the fact that cross-linking is achieved with 0.015 to 0.045% in molar proportions relative to the monomers of ethyleneglycol diglycidyl ether.

10. Polymers according to claim 2, characterized by the fact that the oil phase is cyclohexane.

11. Polymers according to claim 9, characterized by the fact that the oil phase is cyclohexane.

12. Process according to claim 6, characterized by the fact that cross-linking is carried out with 0.015 to 0.045% in molar proportions relative to the monomers of ethyleneglycol diglycidyl ether.

13. Process according to claim 12, characterized by the fact that the oil phase is cyclohexane.

14. Process according to claim 6, characterized by the fact that the oil phase is cyclohexane.

15. In a method of absorbing liquid with a liquid absorbent polymer, the improvement wherein said polymer is in accordance with claim 1.

16. In a method of absorbing liquid with a liquid absorbent polymer, the improvement wherein said polymer is in accordance with claim 2.

17. In a method of absorbing liquid with a liquid absorbent polymer, the improvement wherein said polymer is in accordance with claim 11.

18. In a sanitary product comprising a liquid absorbent polymer, the improvement wherein said polymer is in accordance with claim 1.

19. In a method of producing a water insoluble hydrophilic cross-linked absorbent polymer, in the form of microbeads, containing silica and acrylic acid partially salified by an alkali metal, the improvement comprising the steps of:

polymerizing in a water-in-oil suspension in which an aqueous phase obtained extemporaneously from on the one hand, an aqueous solution containing one or more water soluble polymerization initiators, which are free radical generators, and on the other hand, an aqueous phase containing at a concentration of 50±15% by weight a mixture containing by weight 2 to 25% of colloidal silica and 98 to 75% of acrylic acid of which 60-80% is salified by an alkali metal, is introduced slowly, under agitation, into a totally deoxygenated oil phase maintained at its boiling point and containing a protective colloid, with an aqueous phase to oil phase weight ratio of between 0.8 and 1.2 then, when the polymerization reaction is finished, eliminating 15 to 55% of the water present by azeotropic distillation with recycling of the organic solvent, introducing 0.01 to 0.06%, in molar proportions relative to the monomers, of ethylene glycol diglycidyl ether into the reaction mixture at its boiling point.

continuing the azeotropic distillation of the residual water until a suspension is obtained which has a dry content of 85±10%, and isolating the polymer.

20. Polymers produced by the process of claim 19.

* * * * *